United States Patent
Hayashi

(10) Patent No.: US 7,439,022 B2
(45) Date of Patent: Oct. 21, 2008

(54) NUCLEIC ACIDS FOR DETECTION OF LISTERIA

(75) Inventor: David K. Hayashi, Chicago, IL (US)

(73) Assignee: Kraft Foods Holdings, Inc., Northfield, IL (US)

(*) Notice: Subject to any disclaimer, the term of this patent is extended or adjusted under 35 U.S.C. 154(b) by 237 days.

(21) Appl. No.: 11/153,309

(22) Filed: Jun. 15, 2005

(65) Prior Publication Data

US 2006/0286559 A1    Dec. 21, 2006

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.3; 536/24.32; 536/24.33

(58) Field of Classification Search .............. 435/6, 435/91.2; 536/24.3, 24.32, 24.33
See application file for complete search history.

(56) References Cited

U.S. PATENT DOCUMENTS

2004/0018514 A1*  1/2004  Kunst et al. ................ 435/6

OTHER PUBLICATIONS

Buck e al., BioTechniques, 1999, vol. 27(3), p. 528-536.*
The nucleic acid sequence search report.*

* cited by examiner

*Primary Examiner*—Kenneth R. Horlick
*Assistant Examiner*—Joyce Tung
(74) *Attorney, Agent, or Firm*—Fitch, Even, Tabin & Flannery

(57) ABSTRACT

Isolated nucleic acids and methods for detecting nucleic acid of *Listeria* in a test sample are provided. The isolated nucleic acids may be incorporated into polymerase chain reactions to provide for the rapid detection of *Listeria* in samples.

3 Claims, 6 Drawing Sheets

Figure 1. Alignment of rnpB Sequences from *Listeria*

Figure 2 Alignment of rfn *Listeria* Sequences

|  | 10 | 20 | 30 | 40 | 50 |
|---|---|---|---|---|---|
| L monocytogenes | AAACGAAAA-  | GGTCTGCCAAC | ATCTTCTCCC  | ATCCAGACTAT | ACTGTCGG |
| L innocua       | AAACGAAAA-  | GGTCTGCCAAC | ATCTTCTCCC  | ATCCAGACTAT | ACTGTCGG |
| L seeligeri     | AAACGAAAAA  | GGTCTGTCAAC | ATCTTTCTCCC | ATCCAGACTAT | ACTGTCGG |
| L welshimeri    | AAACGAAAA-  | GGTCTGCCAAC | ATCTTCTCCC  | ATCCAGACTAT | ACTGTCGG |
| L ivanovii      | AAACGAAAA-  | GGTCTGCCAAC | ATCTTCTCCC  | ATCCAGACTAT | ACTGTCGG |
| Consensus       | AAACGAAAAA  | GGTCTGcCAAC | ATCTTCTCCC  | ATCCAGACTAT | ACTGTCGG |

|  | 60 | 70 | 80 | 90 | 100 |
|---|---|---|---|---|---|
| L monocytogenes | TCCTGGAATT | ACACCAGAGT | CAACTGCTAAA | AAAGCAGATCGTGGACTTT |
| L innocua       | TCCTGGAATT | ACACCAGAGT | CAACTGCTAAG | AAAGCAGATCGTGGACTTT |
| L seeligeri     | TCCTGGAATT | ACACCAGAGT | CAACTGCCAAA | AAAGCAGATCGTGGACTTT |
| L welshimeri    | TCCTGGAATT | ACACCAGAGT | CAACTGCTAA- | AAAGCAGATCGTGGACTTT |
| L ivanovii      | TCCTGGAATT | ACACCAGAGT | CAACTGCTAAA | AAAGCAGATCGTGGACTTT |
| Consensus       | TCCTGGAATT | ACACCAGAGT | CAACTGCtAAa | AAAGCAGATCGTGGACTTT |

|  | 110 | 120 | 130 | 140 |
|---|---|---|---|---|
| L monocytogenes | AACCACCGGT | CGGGAATTGCA | CCCTGCCCCG | AAGATGAACG |
| L innocua       | AACCACCGGT | CGGGAATTGCA | CCCTGCCCCG | AAGATGAACG |
| L seeligeri     | AACCACCGGT | CGGGAATTGCA | CCCTGCCCCG | AAGATGAACG |
| L welshimeri    | AACCACCGGT | CGGGAATTGCA | CCCTGCCCCG | AAGATGAACG |
| L ivanovii      | AACCACCGGT | CGGGAATTGCA | CCCTGCCCCG | AAGATGAACG |
| Consensus       | AACCACCGGT | CGGGAATTGCA | CCCTGCCCCG | AAGATGAACG |

Figure 3 Primers and Probe Sequences for rnpB Compared to the *Listeria* rnpB Consensus Sequence
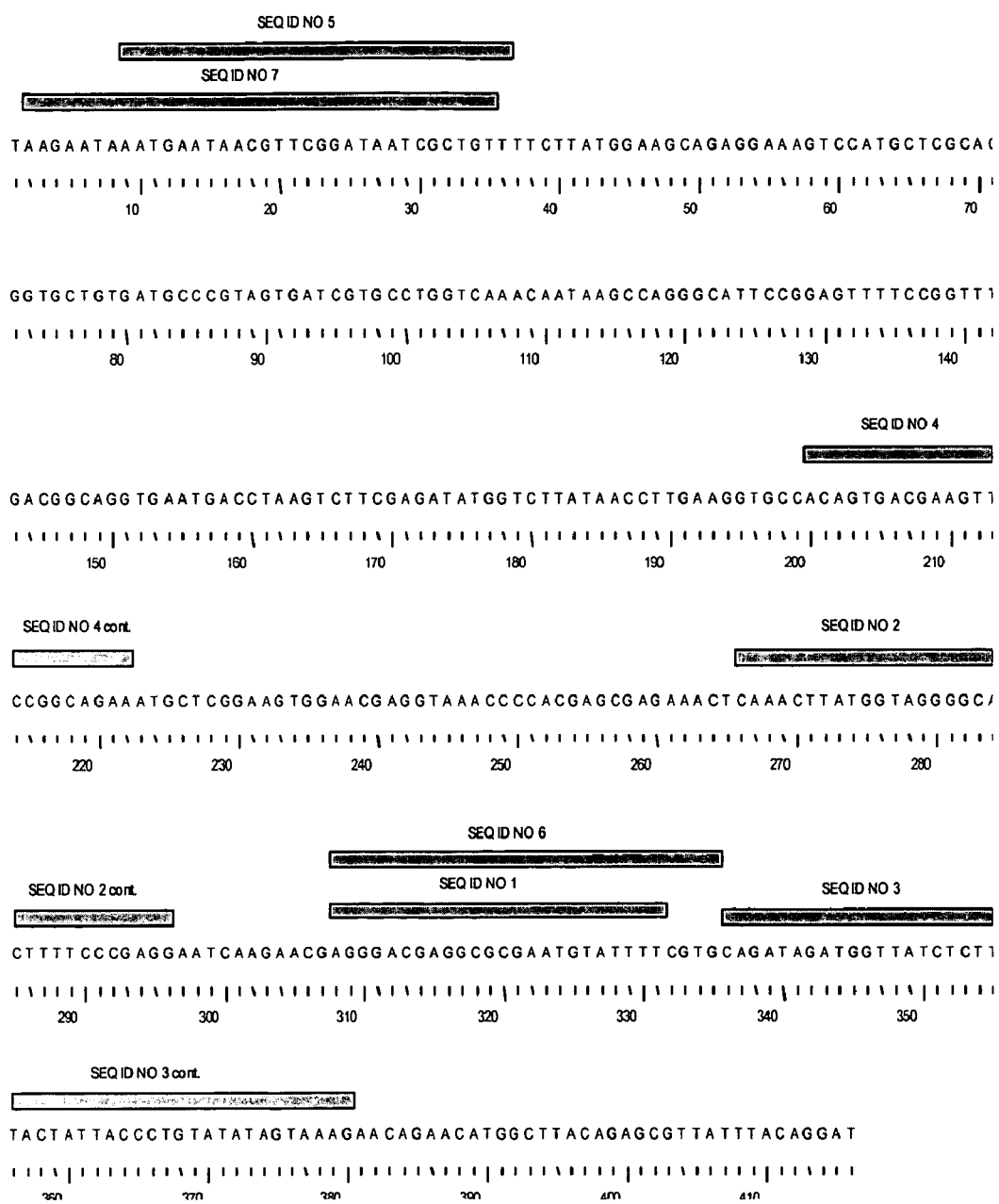

Figure 4 Primers and Probe for rfn Compred to the Consensus Sequences for *Listeria* rfn.

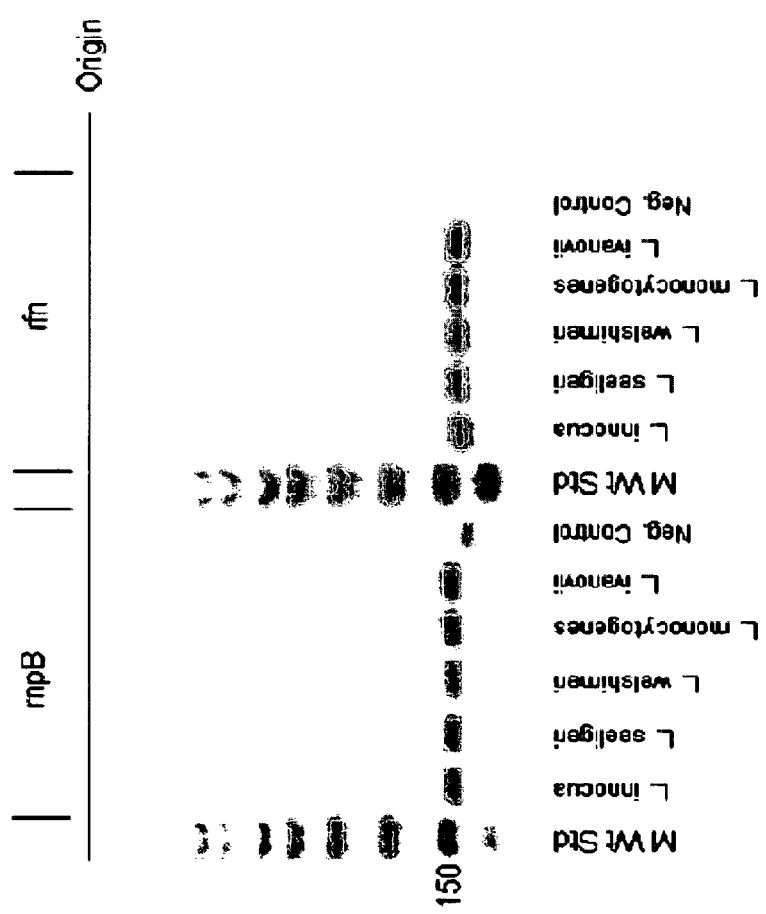
Figure 5. Specificity of rnpB and rfn
Gel photo of the specificity of the primers for both the rnpB and rfn sequences towards the 5 species of *Listeria*

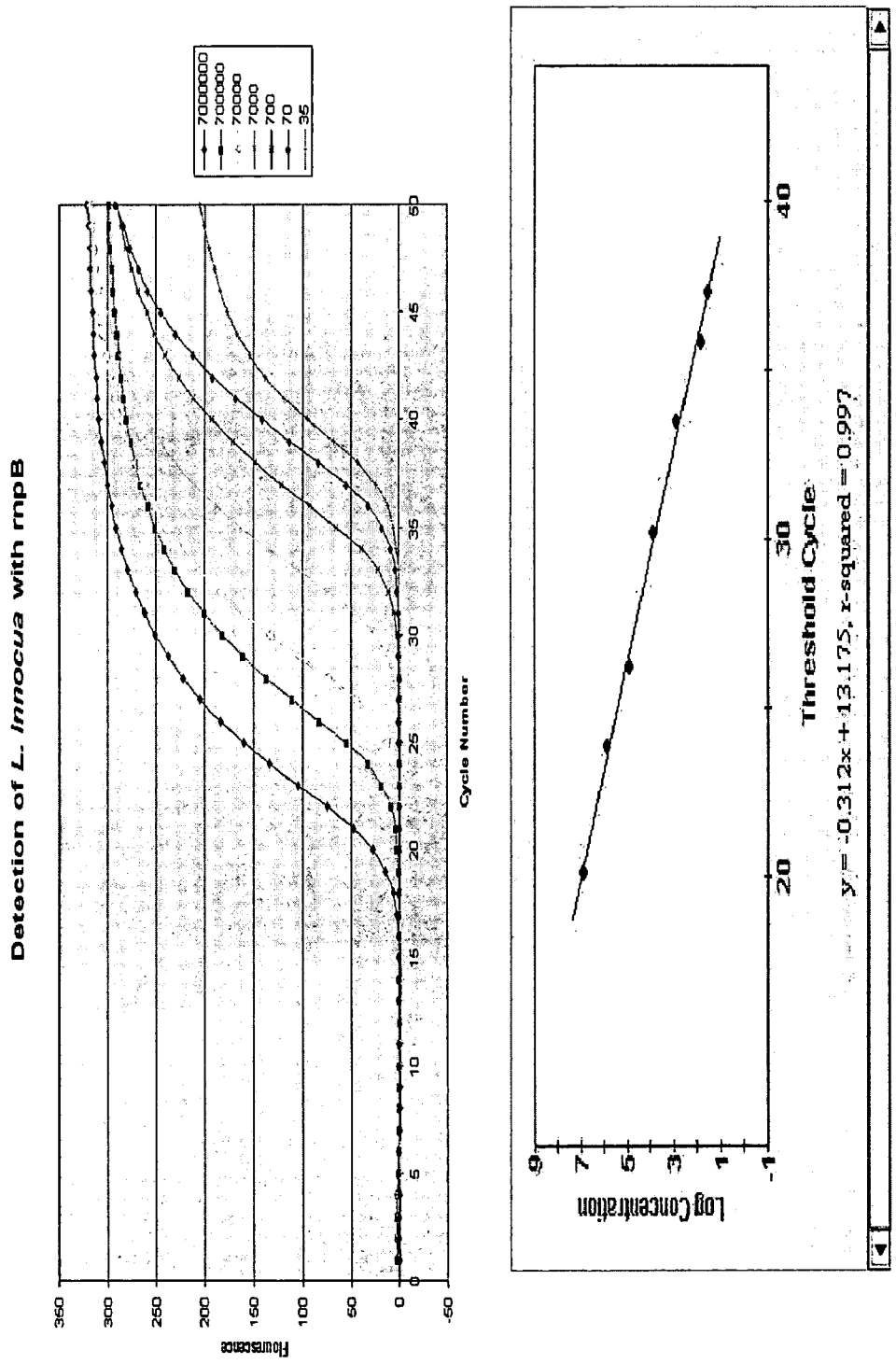
Figure 6. Quantitative Range of real time PCR with rnpB and *Listeria innocua* DNA

NUCLEIC ACIDS FOR DETECTION OF LISTERIA

The invention provides oligonucleotides and methods for the detection of the *Listeria* genus by nucleic acid amplification and/or nucleic acid hybridization.

BACKGROUND

*Listeria* is a genus of ubiquitous bacteria that are gram-positive and non-sporulating and consist essentially of the species *Listeria monocytogenes, L. innocua, L. welshimeri, L. seeligeri* and *L. ivanovii* and *L grayi*. Among these, only some strains of the species *L. monocytogenes* are food borne pathogens for humans, in particular to those with a weakened immune system and for the elderly and the newborn. The most common symptoms of listeriosis are septicemia, meningitis, and miscarriages.

A large number of methods for detecting *Listeria monocytogenes* are known. Conventional detection methods for *L. monocytogenes* require culture enrichment steps to increase the number of *Listeria* cells to a detectable level. After culture enrichment the cells are then allowed to grow out on specific nutrient agarose plates forming individual colonies with distinct morphology allowing for their isolation (Lovett et al., J. Food Protection 50 (1987), 188-192; McClain & Lee, J. Assoc. Off. Anal. Chem. 71 (1988), 660-664). Single colonies are examined for their morphology, biochemical and serological properties. An analysis may take up to 6-8 days to confirm the presence of *Listeria*. Consequently, rapid detection processes for detecting *Listeria*, in particular in foodstuffs or clinical and environmental samples are urgently required.

Various high-speed methods for detecting *Listeria monocytogenes* have been developed. Such methods are based either on immunological methods, the use of polymerase chain reaction (PCR) technology, or on the application of nucleic acid probes.

Some test kits for detection of *Listeria monocytogenes* by means of antibodies are already commercially available. Most of these tests however require at least 10,000 cells for detection. While the immunological tests that are currently on the market only take a few hours, they require a lengthy culture enrichment step(s).

Detection of *Listeria monocytogenes* may be carried out by direct hybridization of probes to microbe-specific DNA or RNA (for example, Datta, A. R. et al., Appl. Environ. Microbiol. 53 (1987), 2256-2259). The major disadvantage of such methods is the low sensitivity, since at least $10^5$-$10^6$ copies of the target nucleic acid are required. This can be compensated for by the amplification of the target sequence, for example using the polymerase chain reaction (PCR). A plurality of PCR methods for detecting *L. monocytogenes* has been described in the literature [for a review see, for example, Jones, D. D. & Bej, A. K. in "PCR Technology, Current Innovations", Griffin, H. G & Griffin, A. M., eds., (1994), 341-365]. See also U.S. Pat. Nos. 4,683,195; 4,683,202 and 4,965,188. Furthermore, the ligase chain reaction [WO publication 89/09835], "self-sustained sequence replication" [EP 329,822], "transcription based amplification system" [EP 310, 229], and Qβ RNA replicase system [U.S. Pat. No. 4,957,858] may be employed for the amplification of nucleic acids.

PCR permits the in vitro amplification of targeted nucleic acids. This increases the sensitivity of detection to fewer cells and subsequently can reduce the length of time needed for culture enrichment. To start the reaction, short nucleic acid fragments (primers) are required. Primers function as pairs with each set encompassing the section of the genome that is to be amplified. Both of the primers are the complementary sequence to the relevant section of the target gene sequence. Since each primer is a complementary sequence it can hybridize with one nucleic acid strand. The formation of this hybridization allows for the enzyme DNA polymerase to direct the synthesis of a complementary strand that is an extension of the primer. Temperature regulated hybridization cycling and the use of thermal stable DNA polymerases are the basis for PCR directed nucleic acid amplification. The choice of the primer pairs determines the specificity of the detection reaction. The use of this process for detecting *L. monocytogenes* is described in Appl. Environmental Microbiology 57, 606-609 (1991), in Letters Appl. Microbiol. 11, 158-162 (1990) and in J. Appl. Bact. 70, 372-379 (1991). More extensive information regarding the details of these processes is available in these publications, PCR Primer A Laboratory Manual CSHL Press(1995) Diffenbach, C. W. and Dveksler, G. S. and Real Time PCR An Essential Guide Horizon Biosciences (2004) Edwards K, Logan, J and Sander, N.

The detection methods described for *L. monocytogenes* are based mainly on targeting genes that play a role in the pathogenicity of *L. monocytogenes*. It is known that some of these genes are located on the chromosome next to each other in a virulence gene cluster (Pathogenicity Islands and Other Mobile Virulence Elements, ASM Press (1999) Kaper, J. B. and Hacker, J.). Since the listeriolysin gene (hlyA) has been recognized as a necessary gene for the pathogenicity of *L. monocytogenes* (Cossart, P. et al., Infect. Immun. 57 (1989), 3629-3636), most of the genotypic detection methods are based on this gene sequence.

Although strains of *Listeria monocytogenes* are the only pathogens to humans, testing for this specific group would be limiting in an effort to identify potential growth habitats for them in food manufacturing facilities. Thus, testing to detect all *Listeria* species is useful in the identification of harborage site. This identification is necessary to allow for through sanitation and the subsequent elimination of *Listeria*.

Detection of groups of bacteria within a given genus requires the identification of gene(s), which have conserved sequences among the target group. Additionally the conserved sequences need to be unique compared to all other non-*Listeria* bacteria to allow for a discriminating test. Genes that have been used for this purpose have typically been of ribosomal origin (J. of Food Protection 1995 58(8) 867-873) or derived from hly (WO9844153) and iap (Applied and Environ Micro 1992 58(8) 2625-2632). The draw-back to ribosomal genes is that they have different copy numbers for different species making quantitation difficult for a genus specific test. The other genes mentioned may have similarity to other sequences that are not of *Listeria* origin, thereby decreasing test specificity. The greater the test specificity of the assay determines which culture enrichment media is appropriate. The use of a non-selective culture enrichment can be employed with a *Listeria* specific DNA assay, since non-*Listeria* would be discriminated for by targeting a unique *Listeria* DNA fragment. Use of selective media can slow the growth and inhibit the recovery of injured *Listeria* requiring a longer incubation period to reach a detectable cell number that relates to an equivalent target DNA copy number. While a non-selective medium can allow for unimpeded optimal growth, ideally single copy genes that have conserved sequence homology within the target *Listeria* genus and span a length of between 100 to 400 base pairs make excellent diagnostic markers.

In view of the above, there is a need for oligonucleotides that can be utilized for diagnostic purposes to detect low levels of the *Listeria* genus. These oligonucleotides can be applied to the many different PCR amplification techniques to provide a quick, sensitive and specific test. The sensitivity and specificity of such a test will make it possible to reduce the incubation time of a culture enrichment step thereby decreasing the overall time needed to get a test result.

SUMMARY

Nucleic acid sequences are provided which can be utilized for the rapid detection of the *Listeria* genus in samples. Genes have been identified which are unique to the genus of *Listeria* and provide targets for rapid nucleic acid assays effective for identifying the presence of *Listeria*. The assays provided can detect as few as 10 copies of said target gene sequences and can provide results within an hour of the start of a polymerase chain reaction. The identified nucleic acid sequence can be incorporated in to a real time quantitative polymerase chain reaction. Each of the oligonucleotide sequences can also be used as probes for hybridization to *Listeria* DNA.

Two gene targets rnpB and rfn are identified for the detection of the *Listeria* genus. Oligonucleotides targeting these genes are provided that can be utilized in the rapid detection of the *Listeria* genus from food, environmental or clinical samples. An important feature of these olignucleotides is their specificity and sensitivity. Usage of these oligonucletides in the polymerase chain reaction can allow for the detection of very low numbers of *Listeria* cells. Their high specificity also allows for the use of non-selective culture enrichment media for the accelerated growth of *Listeria* cells that can subsequently reduce the amount of culture enrichment time necessary to reach detectable concentrations.

Isolated nucleic acid molecule useful in the present invention include:

a. INFORMATION FOR SEQ ID NO 1:
  (I) SEQUENCE CHARACTERISTICS
    1. LENGTH: 24
    2. TYPE: nucleic acid
    3. STRANDEDNESS: single
    4. TOPOLOGY: linear
  (ii) SEQUENCE DESCRIPTION: SEQ ID NO 1

5'-AAAATACATTCGCGCCTCGTCCCT-3';

b) INFORMATION FOR SEQ ID NO 2:
  (I) SEQUENCE CHARACTERISTICS
    1. LENGTH: 30
    2. TYPE: nucleic acid
    3. STRANDEDNESS: single
    4. TOPOLOGY: linear
  (ii) SEQUENCE DESCRIPTION: SEQ ID NO 2

5'-CTCGGGAAAAGTGCCCCTACCATAAGTTTG-3';

c) INFORMATION FOR SEQ ID NO 3:
  (I) SEQUENCE CHARACTERISTICS
    LENGTH: 45
    TYPE: nucleic acid
    STRANDEDNESS: single
    TOPOLOGY: linear
  (ii) SEQUENCE DESCRIPTION: SEQ ID NO 3

5'-CAGATAGATGGTTATCTCTTTACTATTACCCTGTATATAGTAAAG-3';

d) INFORMATION FOR SEQ ID NO 4:
  (I) SEQUENCE CHARACTERISTICS
    LENGTH: 22
    TYPE: nucleic acid
    STRANDEDNESS: single
    TOPOLOGY: linear
  (i) SEQUENCE DESCRIPTION: SEQ ID NO 4

5'-ACAGTGACGAAGTTCCGGCAGA-3' e) INFORMATION FOR SEQ ID NO 5:
  SEQUENCE CHARACTERISTICS
    LENGTH: 28
    TYPE: nucleic acid
    STRANDEDNESS: single
    TOPOLOGY: linear
  SEQUENCE DESCRIPTION: SEQ ID NO 5

5'-AATGAATAACGTTCGGATAATCGCTGTT-3' f) INFORMATION FOR SEQ ID NO 6:
  SEQUENCE CHARACTERISTICS
    LENGTH: 28
    TYPE: nucleic acid
    STRANDEDNESS: single
    TOPOLOGY: linear
  (ii) SEQUENCE DESCRIPTION: SEQ ID NO 6

5'-CACGAAAATACATTTGCGCCTCGTCCCT-3' g) INFORMATION FOR SEQ ID NO 7:
  (I) SEQUENCE CHARACTERISTICS
    LENGTH: 34
    TYPE: nucleic acid
    STRANDEDNESS: single
    TOPOLOGY: linear
  (ii) SEQUENCE DESCRIPTION: SEQ ID NO 7

5'-AAGAATAAATGAATAACGTTCGGATAATCGCTGT-3' h) INFORMATION FOR SEQ ID NO 8:
  (I) SEQUENCE CHARACTERISTICS
    LENGTH: 24
    TYPE: nucleic acid
    STRANDEDNESS: single
    TOPOLOGY: linear
  (ii) SEQUENCE DESCRIPTION: SEQ ID NO 8

5'-ACGAAAAGGTCTGCCAACATCTTC-3';

i) INFORMATION FOR SEQ ID NO 9:
  (I) SEQUENCE CHARACTERISTICS
    LENGTH: 22
    TYPE: nucleic acid
    STRANDEDNESS: single
    TOPOLOGY: linear (ii) SEQUENCE DESCRIPTION: SEQ ID NO 9

5'-CAATTCCCGACCGGTGGTTAAA-3';

j) INFORMATION FOR SEQ ID NO 10:
(I) SEQUENCE CHARACTERISTICS
LENGTH: 33
TYPE: nucleic acid
STRANDEDNESS: single
TOPOLOGY: linear
(ii) SEQUENCE DESCRIPTION: SEQ ID NO 10

5'-TGTAATTCCAGGACCGACAGTATAGTCTGGATG-3';

k) Complements to a), b), c), d), e), f), g), h), i) or j), reverse complements to b, c, d and j and mixtures thereof A method is provided for detecting nucleic acid of the *Listeria* genus in a test sample. The method includes:
(i) providing a test sample containing bacterial nucleic acid, wherein the nucleic acid is accessible to primers or probe;
(ii) providing at least one pair of nucleic acid molecule selected from the group consisting of SEQ ID NO's. 1, 2, 3, 4, 5, 6, and 7, complements of SEQ ID NO's 1, 2, 3, 4, 5, 6, and 7, reverse complements to Seq ID NO's 2, 3 and 4 and mixtures thereof, for use as either a primer for a PCR reaction or a probe for a hybridization reaction; and
(iii) providing at least one pair of nucleic acid molecule selected from the group consisting of SEQ ID NOs. 8, 9 and 10 and complements of SEQ ID NO's 8, 9 and 10, reverse complement of Seq ID No 10 and mixtures thereof, for use as either a primer for a PCR reaction or a probe for a hybridization reaction; and
(iv) performing a PCR reaction and/or a hybridization reaction on said bacterial DNA using said primer or probe.

In another aspect, a method for detecting nucleic acid of *Listeria* in a test sample is provided, the method includes:
(i) providing a test sample containing bacterial nucleic acid, wherein the nucleic acid is accessible to primers or probe(s);
(ii) providing at least one nucleic acid molecule of claim 1 for use as either a primer for a PCR reaction or a probe for a hybridization reaction; and
(iii) performing a PCR reaction and/or a hybridization reaction on said bacterial genomic DNA using said primer or probe to target.

Seq ID NO 13
5'-TAAGAATAAATGAATAACGTTCGGATAATCGCTGTTTTCTTATGGAA
GCAGAGGAAAGTCCATGCTCGCACGGTGCTGTGATGCCCCGTAGTGATCG
TGCCTGGTCAAACAATAAGCCAGGGCATTCCGGAGTTTTCCGGTTTGACG
GCAGGTGAATGACCTAAGTCTTCGAGATATGGTCTTATAACCTTGAAGGT
GCCACAGTGACGAAGTTCCGGCAGAAATGCTCGGAAGTGGAACGAGGTAA
ACCCCACGAGCGAGAAACTCAAACTTATGGTAGGGGCACTTTTCCCGAGG
AATCAAGAACGAGGGACGAGGCGCGAATGTATTTTCGTGCAGATAGATGG
TTATCTCTTTACTATTACCCTGTATATAGTAAAGAACAGAACATGGCTTA
CAGAGCGTTATTTACAGGAT-3
and Seq ID NO 16
5'-AAACGAAAAAGGTCTGCCAACATCTTCTCCCATCCAGACTATACTGT
CGGTCCTGGAATTACACCAGAGTCAACTGCTAAAAAAGCAGATCGTGGAC
TTTAACCACCGGTCGGGAATTGCACCCTGCCCCGAAGATGAACG-3'.

In another aspect, a method for detecting nucleic acid of *Listeria* in a test sample is provided, the method includes:
(i) providing a test sample containing bacterial nucleic acid, wherein the nucleic acid is accessible to primers or probe(s);
(ii) providing at least one nucleic acid molecule which is between 15 and 45 nucleotides in length having a sequence that is identical, complementary or a reverse complement to target Seq ID NO. 13 or 16 for use as either a primer for a PCR reaction or a probe for a hybridization reaction; and
(iii) performing a PCR reaction and/or a hybridization reaction on said bacterial genomic DNA using said primer or probe to target. Seq ID NO 13 and Seq ID NO 16.

BRIEF DESCRIPTION OF FIGURES

FIG. 1 is the alignment of the rnpB sequences from *Listeria*. The alignment shows the degree of homology and the consensus sequence generated from the alignment.

FIG. 2 is the alignment of the rfn sequences from *Listeria*. The alignment shows the degree of homology and the consensus sequence generated from the alignment FIG. 3 is a diagram of the primers and probes for the *Listeria* rnpB target and their placement on the consensus rnpB sequence.

FIG. 4 is a diagram of the primers and probe for the *Listeria* rfn target and their placement on the consensus rfn sequence.

FIG. 5 is a gel image of PCR reactions showing the specificity of rnpB primers (Seq ID NO 1 and Seq ID NO 4) and specificity of rfn primers (Seq ID NO 8 and Seq ID NO 9) towards *L. innocua, L. seeligeri, L. welshimeri, L. monocytogenes* and *L. ivanovii*.

FIG. 6 is diagram of a series of real time reaction using primers (Seq ID NO 1 and Seq ID NO 5) and labeled probe (Seq ID NO 2 with 3' FAM and 5' TAMARA from Operon Biotechnologies) to carry out a Taqman format assay with a range of *L. innocua* DNA. The diagram illustrates the quantitative range of the primers and probes. PCR reaction was carried out on a Smart Cycler (Cepheid) thermal cycler.

DETAILED DESCRIPTION

For the purposes of environmental testing it is ideal to detect all *Listeria* with no distinction for *L. monocyotgenes*.

Definitions

The term "*Listeria*" as used herein, refers to the bacteria classified as such in Bergey's Manual of Systematic Bacteriology (P. H. A. Sneath (ed), 1986, 1234-1245, Williams & Wilkins). Therefore, the term "*Listeria*" as used herein includes *Listeria monocytogenes, Listeria innocua, Listeria seeligeri, Listeria welshimeri, Listeria ivanovii*, and *Listeria grayi*.

As used herein, the term "fragment" or "DNA fragment" is to be understood to mean a single-stranded or double-stranded DNA which can be synthesized, replicated in vitro by, for example, the known polymerase chain reaction method, or replicated in vivo in a bacterium of the *Escherichia coli* type, for example. An analogus term is oligonucleotide. Both are linear oligomers of natural or modified monomers or linkages. These include deoxyribonucleosides, ribonucleosides and others.

Polymerase chain reaction is understood to mean the in vitro amplification of a targeted DNA fragment. Analysis of the amplified DNA fragment can be achieved by gel electrophoresis or in a closed reaction tube format as described by Higuchi et al Biotechnology1993, 11:1026-1030. In this case the use of fluorescent dyes like SYBR Green and SYBR Gold can be used to monitor the reaction. Additionally, many probe formats such as Taqman (U.S. Pat. No. 5,538,848) molecular beacons (U.S. Pat. Nos. 5,925,517 and 6,103,476) and scorpions (U.S. Pat. No. 6,326,145 B1) can be applied. Uses of such techniques are well understood and can be readily carried out by those skilled in the art. This reference and these patents are incorporated herein by reference.

Homology is a term used to describe a comparison of DNA sequences. Those sequences that are identical to each other are homologous. Therefore sequences with a high degree or percent homology to each other are almost identical and differ slightly in their base composition and/or contain deletions or insertions.

Complementary is understood to describe two separate strands of DNA and their ability to form a duplex or double stranded DNA (dsDNA). This is determined by the rules for base pairing between A-T and G-C. In a perfect duplex, the strands are precisely complementary.

Hybridization traditionally is understood as the process by which, under predetermined reaction conditions, two partially or completely complementary single-strands of DNA are allowed to come together in an antiparallel fashion to form a dsDNA duplex with specific and stable hydrogen bonds. The stringency of a particular set of hybridization conditions is defined by the base composition of the probe and target sequences, as well as by the level and geometry of mispairing between the two single strands. Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which hybridization is to take place (e.g., based on the type of assay to be performed) will largely dictate the preferred probes to be employed.

Annealing is understood to mean the formation of a ds DNA. In the context of PCR, temperature is the major parameter directing annealing between primer and probe to the target. Magnesium concentration also is a crucial parameter. Ideally, annealing temperatures between 55° C. and 70° C. and magnesium concentrations of 1 to 8 mM are preferred.

Amplicon refers to the amplified PCR product. This is the target DNA fragment produced with a pair of primers.

Primer/Probe Development

As used herein, primer(s) and probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences.

The identification of a genus specific genetic marker focused on genes that code for small RNA's 100-400 base pairs in length and encode for a required cellular function. Two candidates were chosen 1) The rnpB gene that codes for the catalytic RNA moiety for the enzyme RNase P and 2) the gene rfn that codes for the flavin mononucleotide (FMN) biosysnthesis regulatory switch. Since both these genes code for structural RNA's it was hypothesized they would be conserved and have homologous DNA sequences within the *Listeria* genus yet would have evolved to be different from genetically similar bacteria. Thus, making these genes excellent targets to develop a *Listeria* genus diagnostic test. The rnpB gene for *Bacillus subtilis* subsp. subtilus str 168 can be found in the GenBank database (accession Z99115 region: complement (135022-135422). This sequence was used to probe the *Listeria innocua* Clip 11262 genome using the National Center for Biological Information (NCBI) BLAST search tool. A section of the *B. subtilus* rnpB gene matched at one loci in the *L. innocua* genome. The sequence extending from both the 5' and 3' directions was used as a template to identify primers using the software Oligo 6 (Molecular Biology Insights) to determine the genes from other *Listeria*.

INFORMATION FOR Seq ID NO 11 rnpB sequence primer
   (I) SEQUENCE CHARACTERISTICS
      LENGTH: 24
      TYPE: nucleic acid
      STRANDEDNESS: single
      TOPOLOGY: linear

SEQUENCE DESCRIPTION: SEQ ID NO 11

5'-CGTTTTTGGAAATAAGCTGGACGA-3'

INFORMATION FOR Seq ID NO 12 rnpB sequence primer
   (I) SEQUENCE CHARACTERISTICS
      LENGTH: 22
      TYPE: nucleic acid
      STRANDEDNESS: single
      TOPOLOGY: linear

SEQUENCE DESCRIPTION: SEQ ID NO 12

5'-CAGGCTGAACACCCACCTTAAA-3'

Figure 1:
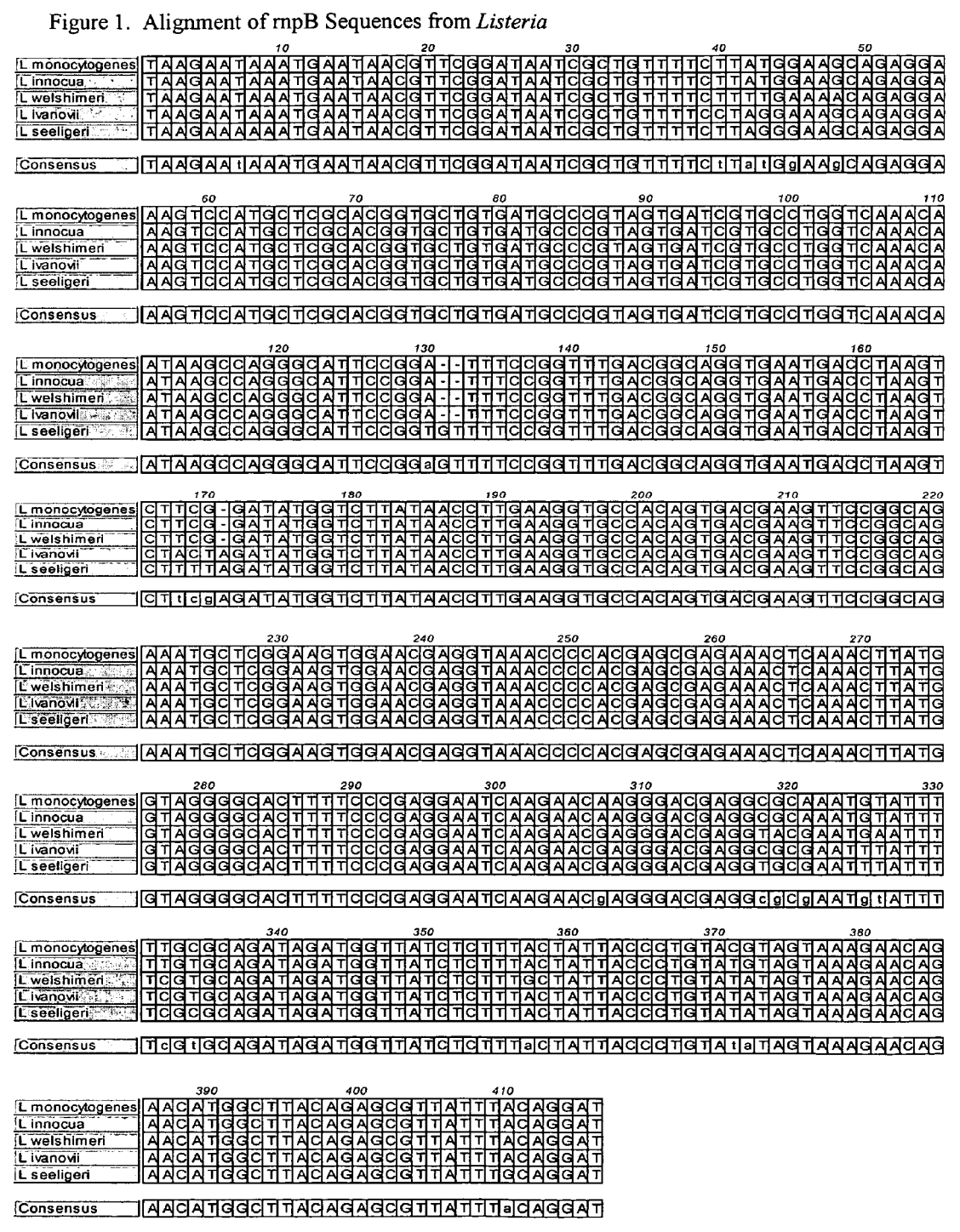

DNA was extracted from *Listeria innocua, Listeria seelgieri, Listeria welshimier, Listeria monocytogenes* and *Listeria ivanovii*. These DNA extracts were used as templates for the identified primers to amplify the target sequence using PCR. The product amplicon was purifed and sequenced with the same primers. The sequences from all five *Listeria* species were aligned using DS gene (Accelrys, Inc) software and a consensus sequence generated (FIG. 1).

INFORMATION FOR Seq ID NO 13 *Listeria* rnpB consensus
   (I) SEQUENCE CHARACTERISTICS
      LENGTH: 416
      TYPE: nucleic acid
      STRANDEDNESS: single
      TOPOLOGY: linear

SEQUENCE DESCRIPTION: SEQ ID NO 13

5'-TAAGAATAAATGAATAACGTTCGGATAATCGCTGTTTTCTTATGGGA

AGCAGAGGAAAGTCCATGCTCGCACGGTGCTGTGATGCCCGTAGTGATCG

TGCCTGGTCAAACAATAAGCCAGGGCATTCCGGAGTTTTCCGGTTTGACG

GCAGGTGAATGACCTAAGTCTTCGAGATATGGTCTTATAACCTTGAAGGT

-continued

GCCACAGTGACGAAGTTCCGGCAGAAATGCTCGGAAGTGGAACGAGGTAA

ACCCCACGAGCGAGAAACTCAAACTTATGGTAGGGGCACTTTTCCCGAGG

AATCAAGAACGAGGGACGAGGCGCGAATGTATTTTCGTGCAGATAGATGG

TTATCTCTTTACTATTACCCTGTATATAGTAAAGAACAGAACATGGCTAC

AGAGCGTTATTTACAGGAT-3'

This sequence was then used as a template to identify primers and probes targeting the rnpB *Listeria* gene using Oligo 6 software. Primers and probes were selected within a region with a high degree of homology (FIG. 3). Homology was required for the bases at the 3' end to insure initiation of DNA polymerase synthesis. BLAST search analysis was performed to confirm that there were no matches to any non-*Listeria* sequences The single copy of rnpB gene codes for the catalytic RNA sub-unit of the enzyme RNase P which is approximately 330 base pairs in length. This gene exhibits a high degree of sequence homology within the *Listeria* genus making for a excellent diagnostic target. Additionally these regions of homology are unique to *Listeria*, allowing for a discriminatory test.

The single copy rfn gene codes for the FMN riboswitch. This gene is approximately 120 base pairs in length. Like the rnpB gene it has the same sequence characteristics of homology and uniqueness within the *Listeria* genus.

The putative rfn gene was identified from the *Listeria innocua* Clip11262 genome (284996-284874) and available on the RNA families database of alignments and CM's (http://www.sanger.ac.uk/Software/Rfam/index.shtml). The same protocol was followed as with the rnpB gene. The primers identified for sequencing the *Listeria* rfn gene are:

INFORMATION FOR Seq ID NO 14 rfn sequencing primer
(I) SEQUENCE CHARACTERISTICS
LENGTH: 26
TYPE: nucleic acid
STRANDEDNESS: single
TOPOLOGY: linear

SEQUENCE DESCRIPTION: SEQ ID NO 14

5'-CACTGGGTAGTAACGGAAATTGTAGC-3'

INFORMATION FOR Seq ID NO 15 rfn sequencing primer
(I) SEQUENCE CHARACTERISTICS
LENGTH: 27
TYPE: nucleic acid
STRANDEDNESS: single
TOPOLOGY: linear

SEQUENCE DESCRIPTION: SEQ ID NO 15

5'-AACCAATACTTAGCGGAATCATTAATC-3'

Alignment of the *Listeria* rfn sequences and generation of a consensus sequence is shown in FIG. 2.

INFORMATION FOR Seq ID NO 16 *Listeria* rfn consensus sequence
(I) SEQUENCE CHARACTERISTICS
LENGTH: 141
TYPE: nucleic acid
STRANDEDNESS: single
TOPOLOGY: linear

SEQUENCE DESCRIPTION: SEQ ID NO 16

5'-AAACGAAAAAGGTCTGCCAACATCTTCTCCCATCCAGACTATACTGT

CGGTCCTGGAATTACACCAGAGTCAACTGCTAAAAAAGCAGATCGTGGAC

TTTAACCACCGGTCGGGAATTGCACCCTGCCCCGAAGATGAACG-3'

Primers and probes selected for rfn using Oligo 6 are illustrated in FIG. 4.

The sequences for both the rnpB and rfn genes have been obtained from the five species (*monocytogenes, innocua, welshimeri, seeligeri* and *ivanovii*) that comprise the *Listeria* genus representing those used in the alignments are as follows.

rnpB from *L. monocytogenes* (SEQ ID NO. 17)
(I) SEQUENCE CHARACTERISTICS
LENGTH: 504
TYPE: nucleic acid
STRANDEDNESS: single
TOPOLOGY: linear

SEQUENCE DESCRIPTION: SEQ ID NO. 17

5'-AAGCTGGACGATAACGAATAGGTATGCTAGTATAAGTAAGTTAAGAA

TAAATGAATAACGTTCGGATAATCGCTGTTTTCTTATGGAAGCAGAGGAA

AGTCCATGCTCGCACGGTGCTGTGATGCCCGTAGTGATCGTGCCTGGTCA

AACAATAAGCCAGGGCATTCCGGATTTCCGGTTTGACGGCAGGTGAATGA

CCTAAGTCTTCGGATATGGTCTTATAACCTTGAAGGTGGGTAGGGGCACT

TTTCCCGAGGAATCAAGAACAAGGGACGAGGCGCAAATGTATTTTTGCGC

AGATAGATGGTTATCTCTTTACTATTACCCTGTACGTAGTAAAGAACAGA

ACATGGCTTACAGAGCGTTATTTACAGGGATTTAATTTAACATTGAAGGC

TGTTTTAGAAGGCCGGAGCGCAAGTTTTAAG-3' rnpB from *L. innocua* (SEQ ID NO. 18)
(I) SEQUENCE CHARACTERISTICS
LENGTH: 508
TYPE: nucleic acid
STRANDEDNESS: single
TOPOLOGY: linear

SEQUENCE DESCRIPTION: SEQ ID NO. 18

5'-TAGCTGGACGATAACGAATAGGTATGCTAGTATAAGTAAGTTAAGAA

TAAATGAATAACGTTCGGATAATCGCTGTTTTCTTATGGAAGCAGAGGAA

AGTCCATGCTCGCACGGTGCTGTGATGCCCGTAGTGATCGTGCCTGGTCA

AACAATAAGCCAGGGCATTCCGGATTTCCGGTTTGACGGCAGGTGAATGA

CCTAAGTCTTCGGATATGGTCTTATAACCTTGAAGGTGCCACAGTGACGA

AGTTCCGGCAGAAATGCTCGGAAGTGGAACGAGGTAAACCCCACGAGCGA

GAAACTCAAACTTATGGTAGGGGCACTTTTCCCGAGGAATCAAGAACAAG

GGACGAGGCGCAAATGTATTTTTGTGCAGATAGATGGTTATCTCTTTACT

ATTACCCTGTATGTAGTAAAGAACAGAACATGGCTTACAGAGCGTTATTT

-continued

ACAGGATTTAATTTAACATTGAAGGCTGTTTTAGAAGGCCGGAGCGCAAG

TTTTAAGGTGT-3' rnpB from *L. seeligeri* (SEQ ID NO. 19)
(I) SEQUENCE CHARACTERISTICS
LENGTH: 426
TYPE: nucleic acid
STRANDEDNESS: single
TOPOLOGY: linear

SEQUENCE DESCRIPTION: SEQ ID NO. 19

5'-TTAAGAAAAAATGAATAACGTTCGGATAATCGCTGTTTTCTTAGGGA

AGCAGAGGAAAGTCCATGCTCGCACGGTGCTGTGATGCCCGTAGTGATCG

TGCCTGGTCAAACAATAAGCCAGGGCATTCCGGTGTTTTCCGGTTTGACG

GCAGGTGAATGACCTAAGTCTTTTAGATATGGTCTTATAACCTTGAAGGT

GCCACAGTGACGAAGTTCCGGCAGAAATGCTCGGAAGTGGAACGAGGTAA

ACCCCACGAGCGAGAAACTCAAACTTATGGTAGGGGCACTTTTCCCGAGG

AATCAAGAACGAGGGACGAGGTGCGAATTTATTTTCGCGCAGATAGATGG

TTATCTCTTTACTATTACCCTGTATATAGTAAAGAACAGAACATGGCTTA

CAGAGCGTTATTTGCAGGATGAATTTAAC-3' rnpB from *L welshimeri* (SEQ ID NO. 20)
(I) SEQUENCE CHARACTERISTICS
LENGTH: 504
TYPE: nucleic acid
STRANDEDNESS: single
TOPOLOGY: linear

SEQUENCE DESCRIPTION: SEQ ID NO. 20

5'-ATAGCTGGACGATAACGACTAGGTGTGCTAGTATAAGTAAGTTAAGA

ATAAATGAATAACGTTCGGATAATCGCTGTTTTCTTTTGAAAACAGAGGA

AAGTCCATGCTCGCACGGTGCTGTGATGCCCGTAGTGATCGTGCCTGGTC

AAACAATAAGCCAGGGCATTCCGGATTTCCGGTTTGACGGCAGGTGAATG

ACCTAAGTCTTCGGATATGGTCTTATAACCTTGAAGGTGCCACAGTGACG

AAGTTCCGGCAGAAATGCTCGGAAGTGGAACGAGGTAAACCCCACGAGCG

AGAAACTCAAACTTATGGTAGGGGCACTTTTCCCGAGGAATCAAGAACGA

GGGACGAGGTACGAATGAATTTTCGTGCAGATAGATGGTTATCTCTTTGC

TATTACCCTGTATATAGTAAAGAACAGAACATGGCTTACAGAGCGTTATT

TACAGGATTAATTTAACATTGAAGGCTGTTTTAGAAGGCCGGAGCGCAAG

TTTTAAG-3' rnpB from *L. ivanovii* (SEQ ID NO. 21)
(I) SEQUENCE CHARACTERISTICS
LENGTH: 411
TYPE: nucleic acid
STRANDEDNESS: single
TOPOLOGY: linear

SEQUENCE DESCRIPTION: SEQ ID NO. 21

5'-AAATGAATAACGTTCGGATAATCGCTGTTTTCCTAGGAAAGCAGAGG

AAAGTCCATGCTCGCACGGTGCTGTGATGCCCGTAGTGATCGTGCCTGGT

CAAACAATAAGCCAGGGCATTCCGGATTTCCGGTTTGACGGCAGGTGAAT

GACCTAAGTCTACTAGATATGGTCTTATAACCTTGAAGGTGCCACAGTGA

CGAAGTTCCGGCAGAAATGCTCGGAAGTGGAACGAGGTAAACCCCACGAG

CGAGAAACTCAAACTTATGGTAGGGGCACTTTTCCCGAGGAATCAAGAAC

GAGGGACGAGGCGCGAATTTATTTTCGTGCAGATAGATGGTTATCTCTTT

ACTATTACCCTGTATATAGTAAAGAACAGAACATGGCTTACAGAGCGTTA

TTTACAGGATGAAT-3' rfn from *L. monocytogenes* (SEQ ID NO. 22)
(I) SEQUENCE CHARACTERISTICS
LENGTH: 485
TYPE: nucleic acid
STRANDEDNESS: single
TOPOLOGY: linear

SEQUENCE DESCRIPTION: SEQ ID NO. 22

5'-CCAAGAACCGCCACACTTACAAAAACCTTCATTGAATAATTCTTCAT

TGTCATTTCTCCCTTGATGTTCACCAAGAAGCGAGTGACATCACTAGACG

AATGCAACCCAAGCAAATAAAAAACCTCAACTGAAAAGAGTTGAGGGAGA

GTTTGTGAATGAATAAACAAGAACCGGATACTCAAATAAGCATCACAGCT

TGCTAACACATGCTCGTGAAGACAAACGAAAAGGTCTGCCAACATCTTCT

CCCATCCAGACTATACTGTCGGTCCTGGAATTACACCAGAGTCAACTGCT

AAAAAAGCAGATCGTGGACTTTAACCACCGGTCGGGAATTGCACCCTGCC

CCGAAGATGAACGAATATTTTATTACAATTTTCATTTTACCATGAAAAAA

ATTTTTGGCAAGCACTTTTGTATATTTTTTCACGTAAGCGCTTTGTATCT

AAATTAAATAAAAACTAGCTGCTTAGCTAGTTTTTATT-3' rfn from *L. innocua* (SEQ ID NO. 23)
(I) SEQUENCE CHARACTERISTICS
LENGTH: 490
TYPE: nucleic acid
STRANDEDNESS: single
TOPOLOGY: linear

SEQUENCE DESCRIPTION: SEQ ID NO. 23

5'-AATGCTAAAGTACCAAAGAACCGCCACACTTACAAAAACCTTCATTG

AATAATTCTTCATTGTCATTTCTCCCTTGATGTTCACCAAGAAGCGAGTG

ACATCACTAAACGAATGCAACCCAAGCAAATAAAAAACCTCAACTAAAAA

AAGTCGAGGGAGAGTTTGTGATTAATTAAACAAGCACTGAATACTCAAAT

AAGCATCACAGCTTGCTAACACATGCTCGTGAAGACAAACGAAAAGGTCT

GCCAACATCTTCTCCCATCCAGACTATACTGTCGGTCCTGGAATTACACC

AGAGTCAACTGCTAAGAAAGCAGATCGTGGACTTTAACCACCGGTCGGGA

ATTGCACCCTGCCCCGAAGATGAACGAATATTTTATTACAATTTTCATTT

-continued

TACCATGAAAATATTTTTTCGCAAGTCCTTTTGTATATTTTTTCACGTAA

GCGCTTTCTTAGTTACAAAAATAAAAACCACGATGATTATCTG-3' rfn from *L. seeligeri* (SEQ ID NO. 24)
(I) SEQUENCE CHARACTERISTICS
  LENGTH: 460
  TYPE: nucleic acid
  STRANDEDNESS: single
  TOPOLOGY: linear

SEQUENCE DESCRIPTION: SEQ ID NO. 24

5'-TCCTAGCACCGCCACACTTACAAAAACCTTCATTGAATAATTCTTCA

TTGTCATTTCTCCCTTGATGTTCATCAAAAGAAGCGAGTGACATCACTTA

ACGAATGCAACCCAAGCAAATAAAAAACCTCAACTAAAAAAGTTGAGGGA

GAGTTTGTGAATAAATAAACAAACGTTAGATACTCAAATAAGCATCTTAG

CTTGCTCACACATGCTCGTGAAGACAAACGAAAAGGTCTGTCAACATCT

TCTCCCATCCAGACTATACTGTCGGTCCTGGAATTACACCAGAGTCAACT

GCCAAAAAAGCAGATCGTGGACTTTAACCACCGGTCGGGAATTGCACCCT

GCCCCGAAGATGAACGAATATTTTCTTACAATTTTTATTTTACCATGAAT

AAATATTTTCGCAAGCCCTTTTGTATATTTTTTCACGTAAGCGCTTTCTT

ATATAAACAAACA-3' rfn from *L. welshimeri* (SEQ ID NO. 25)
(I) SEQUENCE CHARACTERISTICS
  LENGTH: 451
  TYPE: nucleic acid
  STRANDEDNESS: single
  TOPOLOGY: linear

SEQUENCE DESCRIPTION: SEQ ID NO. 25

5'-ACGCTTACAAAAACCTTCATTGAATAATTCTTCATTGTCATTTCTCC

CTTGATGTTCACCAAGAAGCGAGTGACATCACTTAACGAATGCAACCCAA

GCAAATAAAAAACCTCAACTAAAAAAAGTTGAGGGAGAGTTTGTGAATAA

ATAAACAAGAACAGAATACTTAAATAAGCATCCAAGCTTGCTACCACATG

CTCGTGAAGACAAACGAAAAGGTCTGCCAACATCTTCTCCCATCCAGACT

ATACTGTCGGTCCTGGAATTACACCAGAGTCAACTGCTAAAAAGCAGATC

GTGGACTTTAACCACCGGTCGGGAATTGCACCCTGCCCCGAAGATGAACG

AATATTTTATTACAATTTTTATTTTACCATGAAAAATTTTTTCGCAAGC

CATTTTGTATATTTTTTCACGTAAGCGCTTTCTTATAAAAGAAACGAAAA

ACCA-3' rfn from *L. ivanovii* (SEQ ID NO. 26)
(I) SEQUENCE CHARACTERISTICS
  LENGTH: 431
  TYPE: nucleic acid
  STRANDEDNESS: single
  TOPOLOGY: linear

SEQUENCE DESCRIPTION: SEQ ID NO. 26

5'-GAATAATTCTTCATTGTCATTTCTCCCTTGATGTTCACCAAGAAGGT

GAGTGACGTCATTTAACGAATGCAACCCAAGCAAATAAAAAACCTCAACT

AAAAAAAGTTGAGGGAGAGTTTGTGAAACAATAAACAAACATTAGATGCT

CAAATAAACATCACAGCTTGCTAACACATGCTCGTGAAGACAAACGAAAA

GGTCTGCCAACATCTTCTCCCATCCAGACTATACTGTCGGTCCTGGAATT

ACACCAGAGTCAACTGCTAAAAAAGCAGATCGTGGACTTTAACCACCGGT

CGGGAATTGCACCCTGCCCCGAAGATGAACGAATATTTTCTTACAAATTT

TATTTTACCATGAATAAATATTTTCGCAAGTCCTTTTGTATATTTTTCA

CGTGAGCGTTTTCTTAATTATTCCAATAAAAAACC-3'

Samples

Food product(s), those of the ready to eat type such as meats and dairy product, environmental samples such as sponges and swabs as well as clinical samples can be used for testing. These above-mentioned samples can be placed in a suitable culture enrichment media to increase the number of *Listeria* cells. The culture enrichment protocol as outlined in the Bacteriological Analytical Manual (BAM)8th ed. AOAC 1998 Chapter 10 would be suitable and is incorporated herein by reference. The inoculated culture enrichment media can then be used to extract the DNA for PCR.

DNA can be extracted following Example 1 (template preparation) or the use of many commercially available genomic DNA extraction kits (Promega, Qiagen, Dynal and Invitrogen are some suppliers).

Detection Methods

To detect *Listeria,* nucleic acids are first released from cells contained in a sample or bacterial culture to be investigated. *Listeria* may be detected by means of nucleic acid hybridization and/or by PCR using specific oligonucleotide primers and/or probes, directly to detect *Listeria*-specific nucleic acid sequences in the sample to be investigated. Various methods known to the skilled worker are suitable for this purpose such as, for example, Southern blotting.

PCR may be used alone or in combination with probes to detect the presence of *Listeria* in a sample. In this connection, specific amplified molecules are formed only if *Listeria* DNA/RNA is present. A detection reaction (following or during the amplification reaction) using the nucleic acid molecules according to the invention as primers and/or probes can increase the specificity of the detection method.

According to the invention, it is possible to use various methods in order to detect the amplification products generated in the methods. These include, visualization by means of gel electrophoresis, hybridization of probes to immobilized reaction products [coupled to nylon or nitrocellulose filters (Southern blots) or, for example, to beads and microtiter plates] and hybridization of the reaction products to immobilized probes (for example reverse dot blots or probes coupled to beads on or in microtiter plates). In addition, it is possible to use methods in which one or more of the nucleic acid molecules according to the invention can, as probes, qualitatively and quantitatively detect amplification products during the PCR reaction ("real time").

According to the invention, there is a large number of possibilities for the oligonucleotides (e.g. probes and primers) to be possibly labeled or modified for the direct or indirect detection methods described. Thus, said oligonucleotides may contain, for example, radioactive, colored, fluorescent or otherwise modified or modifying groups, for example antibodies, antigens, enzymes or other substances with affinity to enzymes or enzyme complexes. Probes for PCR may be labeled with fluorescent molecules and molecules that can quench their fluorescence to employ florescence resonance energy transfer. Probes and primers may be either naturally occurring or synthetically produced double-stranded or single-stranded DNA or RNA or modified forms of DNA or RNA such as, for example, PNA (in these molecules the sugar units have been exchanged for amino acids or peptides). Individual or a plurality of nucleotides of the probes or primers according to the invention may be replaced by analogous building blocks (such as, for example, nucleotides which are not naturally present in the target nucleic acid). In particular, up to 20% of at least 10 successive nucleotides of a nucleotide chain, in particular 1 or 2 nucleotides, may be replaced by analogous building blocks known per se for probes and/or primers.

The resulting nucleic acids may be analyzed directly with probes or may be subjected to PCR. Direct analysis of samples may be conducted with probes (SEQ. ID. Nos. 1, 2, 3, 4, 5, 6, 7, 8, 9 and 10 and their reverse complements) using known techniques. Alternatively, PCR may be used to amplify target sequenced followed by the use of probes. In another alternative aspect, PCR may be using a primer pair with a probe and/or a unimolecular primer probe that hybridizes to the amplicon to detect the presence of Listeria nucleic acids.

Detection Kits

An assay kit for detection of Listeria may include any of the nucleic acid sequences described herein along with appropriate reagents and vials to carry out an analysis.

EXAMPLES

Example 1

Template and PCR Reactions

Template Preparation

1. A 1 ml culture enrichment (Sample containing Listeria (environmental sponge or swab) is inoculated into Tryptic Soy broth and incubated 12 hours at 30° C. is centrifuged (Eppendorf 5417C) at 14,000 rpm for 5 minutes. The supernatant is decanted and the pellet is resuspended in 1 ml of 0.9% NaCl.

2. The suspension is centrifuged at 14,000 rpm for 5 minutes. The supernatant is decanted and the pellet is resuspended in 100 µl Butterfield's Buffer.

3. The 100 ml suspension is added to a Bead Mill tube along with 1 ml of Solution #1 (10 mM Tris-HCl, pH 8.0, 1 mM EDTA, 0.1% sodium dodecyl sulfate, and 1.5M guanidiune thiocyanate). The Bead Mill tube contained 0.9 g. 0.1 mm zirconiasilica beads.

4. Homogenization of the sample in the Bead Mill tube is conducted on a Mini-Beadbeater-8 (Biospec) for 4 minutes.

5. The Bead Mill tube is centrifuged at 14,000 rpm for 1 minute.

6. 650 µl of supernatant is removed from the Bead Mill tube into a centrifuge tube and mixed with 65 µl of 3M Sodium Acetate (pH 5.2) followed by vortexing.

7. 450 µl of isopropanol is added and the mixture is vortexed.

8. The tube is held in an ice bath for 1 hour and then is centrifuged at 14,000 rpm for 5 minutes.

9. The supernatant is decanted and the pellet is resuspended with addition of 500 µl of 70% ethanol followed by vortexing.

10. The tube is held in an ice bath for 1 hour and then is centrifuged at 14,000 rpm for 5 minutes.

11. The supernatant is decanted and the pellet is air dried.

12. The pellet is resuspended in 200 µl of 10 mM Tris at pH 8.0 to provide a template for subsequent PCR.

PCR Reactions

A standard PCR reaction is set up as follows.
1 unit TAQ DNA Polymerase
4 mM MgCl$_2$
20 mM Tris-HCl pH 8.4
50 mM KCl
200 µM dNTP
0.5 µM forward primer (SEQ. ID. NO. 1)
0.5 µM reverse primer (SEQ. ID. NO. 4)
2 µl template (as prepared above)
50 µl reaction volume The PCR reaction can be run on an Applied BioSystems GenAmp 9700 or equivalent system. Cycling parameters for the PCR of Listeria are as follows.

1. 94° C. for 5 minutes.
2. 62° C. for 12 minutes.
3. 94° C. for 10 seconds.
4. 72° C. for 3 minutes.

Hold at 4° C.

Steps 2 and 3 are repeated 50 times.

The sample reactions are analyzed on agarose gel electrophoresis using standard techniques where the presence of the target Listeria DNA can be visualized. A band will be present at the appropriate size indicating detection of the Listera. A gel photo of the specificity of the primers for both the rnpB and rfn sequences towards the 5 species of Listeria is shown in FIG. 5.

Example 2

Real Time PCR Quantitative Range

Real time PCR Reaction Set Up
25 µl reaction volume
2 µl DNA (see Example 1, Template preparation)
1.5 units TAQ DNA polymerase
25 mM HEPES
200 µM dNTP
500 nM forward primer (SEQ. ID. NO. 1)
500 nM µM reverse primer (SEQ. ID. NO. 5)
64 nM probe (SEQ. ID. NO. 2)

The Taqman probe design was utilized to demonstrate the potential for the identified oligonucleotide primers and probe to work in a real time PCR format. The probe has a melting temperature approximately 5° C. higher than the primers. Therefore the probe will be hybridized to the template DNA before the primers. The Taq DNA polymerase enzyme will encounter the hybridized probe while synthesizing the complimentary strand. The Taq has a 5'-3' hydrolysis activity that will degrade the probe. When this happens the fluorescent dye goes from a quenched state to a fluorescent state. This enables the tracking of the production of the diagnostic amplicon. The concentration of the target (Listeria) can be calculated based on the time (number of cycles, point where the fluorescence goes above a set threshold value) when the fluorescence increases which represent the synthesis of the amplicon.

Real Time PCR Cycling Parameters
1. 95° C. for 5 minutes.
2. 65° C. for 40 seconds with Fluorescence Detection.
3. 95° C. for 10 seconds
Steps 2 and 3 are repeated 50 times Real Time PCR reactions are run on a Cepheid Smart Cycler. An illustration of real time PCR with Taqman probe is shown in FIG. 6. Serial dilutions of the DNA template were carried out. Equivalent colony forming units were calculated based on the starting material used.

Example 3

Real Time PCR Sensitivity and Specificity

Real Time PCR Reaction Set Up
25 µl reaction volume
2 ul DNA (see Example 1, Template preparation)
1.5 units TAQ DNA polymerase
25 mM HEPES
200 µM dNTP
750 nM forward primer (SEQ. ID. NO. 6)
750 nM reverse primer (SEQ. ID. NO. 7)
64 nM probe (SEQ. ID. NO. 2)
Real Time PCR Cycling Parameters
1. 95° C. for 5 minutes.
2. 60° C. for 2 seconds.
3. 66° C. for 40 seconds with Fluorescence Detection
4. 95° C. for 2 seconds
Steps 2, 3 and 4 are repeated 40 times The proceed to
5. 66° C. for 40 seconds with Fluorescence Detection
6. 95° C. for 2 seconds
Steps 5 and 6 repeated 10 times Real Time PCR reactions are run on a Cepheid Smart Cycler. Serial dilution of DNA extract were used as templates. DNA concentration were based on Pico Green measurements with a lambda DNA standard. Table 1 represents the finding from the five *Listeria* species.

Table 1 shows results from the real time PCR reaction targeting the rnpB sequence against DNA from *L. innocua, L. seeligeri, L. welshimeri, L. monocytogenes* and *L. ivanovii* using primers (Seq ID NO 6 no AND Seq ID NO 7) and labeled probe (Seq ID NO 2 with 5' FAM and 3' TAMARA from Operon Biotechnologies) Results are expressed as Cycle Threshold values (Ct). Thresholds were set at 30 units. Cycling conditions are noted in the table. Reactions were carried out on a Smart Cycler.

TABLE 1

Real time PCR Sensitivity and Specificity with rnpB

| | Template conc. | Trial 1 $C_t$ | Trial 2 $C_t$ | Trial 3 $C_t$ |
| --- | --- | --- | --- | --- |
| *L innocua* | 230 fg | 35.08 | 35.60 | 35.29 |
| | 23 fg | 38.47 | 38.44 | 40.30 |
| | 2.3 fg | 44.13 | 47.52 | 0.00 |
| *L seeligeri* | 230 fg | 36.44 | 35.69 | 36.09 |
| | 23 fg | 38.15 | 39.80 | 40.16 |
| | 2.3 fg | 0.00 | 0.00 | 44.11 |
| *L welshimeri* | 230 fg | 37.19 | 36.51 | 37.17 |
| | 23 fg | 38.92 | 41.42 | 42.35 |
| | 2.3 fg | 47.09 | 0.00 | 47.37 |
| *L monocytogenes* | 230 fg | 34.93 | 35.94 | 35.73 |
| | 23 fg | 39.95 | 39.59 | 39.61 |
| | 2.3 fg | 44.83 | 0.00 | 0.00 |
| *L ivanovii* | 230 fg | 34.53 | 35.27 | 35.85 |
| | 23 fg | 39.43 | 38.79 | 38.77 |
| | 2.3 fg | 40.07 | 0.00 | 0.00 |

Example 3

Primer Cross Reaction Testing

Primer sequences are also compared to the GenBank database to determine if there are any matches found to bacteria other than *Listeria*. Then the primers are tested against DNA extracts from bacteria which are closely related to *Listeria*. A diagnostic DNA (amplicon) band is not present on the gel in samples where no cross-reaction occurs. A primer pair that demonstrates no cross-reaction is then combined with a probe and tested on real time PCR.

Real Time PCR Reaction Set Up
  25 µl reaction volume
  2 ul DNA (see Example 1, Template preparation)
  1.5 units TAQ DNA polymerase
  25 mM HEPES
  200 µM dNTP
  750 nM forward primer (SEQ. ID. NO. 6)
  750 nM reverse primer (SEQ. ID. NO. 7)
  64 nM probe (SEQ. ID. NO. 2)
Real Time PCR Cycling Parameters
  1. 95° C. for 5 minutes.
  2. 60° C. for 2 seconds.
  3. 66° C. for 40 seconds with Fluorescence Detection
  4. 95° C. for 2 seconds
  Steps 2, 3 and 4 are repeated 40 times Then proceed to
  5. 66° C. for 40 seconds with Fluorescence Detection
  6. 95° C. for 2 seconds
  Steps 5 and 6 repeated 10 times.

Real Time PCR reactions are run on a Cepheid Smart Cycler. Table 2 illustrates results from cross reaction testing using primers (Seq ID NO 6 and Seq ID NO 7) and labeled probe (Seq ID NO 2 with 3' FAM and 5' TAMARA from Operon Biotechnologies) 0 value indicates no fluorescent signal was detected higher than the threshold of 30 units indicating a negative test result.

Table 2 shows results from real time PCR reactions targeting the rnpB sequence against DNA (2 ul DNA extract of 24 hour cultures in tryptic soy broth following protocol outlined in example 1) from bacteria which are genetically similar to *Listeria* using primers (SEQ ID NO 6 and Seq ID NO 7) and probe (Seq ID NO 2). Results are expressed as Cycle Threshold values (Ct). Thresholds were set at 30 units. Reactions were carried out on a Smart Cycler.

TABLE 2

Multiplex real time PCR with rnpB and rfn

| Equivalent cfu | L. monocytogenes mpB C$_t$ | rfn C$_t$ | Equivalent cfu | L. innocua mpB C$_t$ | rfn C$_t$ | Equivalent cfu | L. seeligeri mpB C$_t$ | rfn C$_t$ | Equivalent cfu | L. welshimeri mpB C$_t$ | rfn C$_t$ | Equivalent cfu | L. ivanovii mpB C$_t$ | rfn C$_t$ |
|---|---|---|---|---|---|---|---|---|---|---|---|---|---|---|
| 5,000 | 31.50 | 31.49 | 7,000 | 30.39 | 30.70 | 12,000 | 30.55 | 31.68 | 7,000 | 31.20 | 29.24 | | 28.52 | 28.75 |
| 500 | 36.23 | 35.27 | 700 | 33.81 | 33.80 | 1,200 | 33.61 | 34.67 | 700 | 34.58 | 32.59 | | 31.43 | 31.67 |
| 50 | 37.99 | 38.12 | 70 | 37.86 | 36.76 | 120 | 37.62 | 38.23 | 70 | 37.93 | 36.38 | | 35.36 | 35.63 |
| 5 | 41.67 | 39.86 | 7 | 39.72 | 42.34 | 12 | 41.54 | 40.25 | 7 | 48.61 | 39.97 | | 37.41 | 37.80 |

Example 4

Real Time PCR Multiplex Detection of rnpB and rfn

Real Time PCR Reaction Set Up
25 µl reaction volume
2 ul DNA (see Example 1, Template preparation)
1.5 units TAQ DNA polymerase
25 mM HEPES
200 µM dNTP
500 nM forward rnpB primer (SEQ. ID NO. 1)
500 nM reverse rnpB primer (SEQ. ID. NO. 5)
64 nM rnpB probe (SEQ. ID. NO. 2)
500 nM forward rfn primer (SEQ. ID. NO. 8)
500 nM reverse rfn primer (SEQ. ID. NO. 9)
64 nM rfn probe (SEQ. ID. NO. 10)
Real Time PCR Cycling Parameters
1. 95° C. for 5 minutes.
2. 65° C. for 40 seconds with Fluorescence Detection.
3. 95° C. for 10 seconds
Steps 2 and 3 are repeated 50 times Real Time PCR reactions are run on a Cepheid Smart Cycler. Serial dilutions of the DNA template were carried out. Equivalent colony forming units were calculated based on the starting material used. Results are shown in Table 3.

Table 3 are results from the real time PCR reaction targeting bothe rnpB the rfn sequence against DNA from L. innocua, L. seeligeri, L. welshimeri, L. monocytogenes and L. ivanovii using primers (Seq ID NO 1 and Seq ID NO 4) and labeled probe (Seq ID NO 2 with 5' FAM and 3' TAMARA from Operon Biotechnologies) for rnpB and using primers (Seq ID NO 8 and Seq ID NO 49) and labeled probe (Seq ID NO 10 with 5' Cy3 and 3' Black Hole Quencher 2 from Operon Biotechnologies) for rnpB. Results are expressed as Cycle Threshold values (Ct). Thresholds were set at 30 units for Seq ID NO 2 and 15 units for Seq ID NO 10. Reactions were carried out on a Smart Cycler.

TABLE 3

Real Time PCR with rnpB testing Cross Reactivity with Closely Related Bacteria to Listeria

| Organism | rnpB C$_t$ |
|---|---|
| Staphylococcus epidermidis | 0 |
| Staphylococcus aureus | 0 |
| Staphlococcus carnosus | 0 |
| Enterococcus faecium | 0 |
| Enterococcus faecalis | 0 |
| Pediococcus | 0 |
| Streptocococcus bovis | 0 |
| Macrococcus caseolyticus | 0 |
| Leuconostoc | 0 |
| Lactococcus lactis | 0 |
| Lactococcus I diacetylactis | 0 |
| Lactobacillus plantarum | 0 |
| Lactobacillus bulgaricus | 0 |
| Lactobacillus fermentum | 0 |
| Lactobacillus casei (1 ng) | 0 |
| Lactobacillus brevis | 0 |
| Bacillus lichenformis | 0 |
| Bacillus cereus | 0 |
| Bacillus thuringiensis | 0 |
| Bacillus subtilis | 0 |
| Bacillus megaterium | 41.33 |

SEQUENCE LISTING

<160> NUMBER OF SEQ ID NOS: 26

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
aaaatacatt cgcgcctcgt ccct                                           24

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
ctcgggaaaa gtgcccctac cataagtttg                                    30

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
cagatagatg gttatctctt tactattacc ctgtatatag taaag                   45

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
acagtgacga agttccggca ga                                            22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
aatgaataac gttcggataa tcgctgtt                                      28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
cacgaaaata catttgcgcc tcgtccct                                      28

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
aagaataaat gaataacgtt cggataatcg ctgt                               34

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
acgaaaaggt ctgccaacat cttc                                          24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
caattcccga ccggtggtta aa                                            22

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
tgtaattcca ggaccgacag tatagtctgg atg                                33

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
cgttttggga aataagctgg acga                                          24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
caggctgaac acccacctta aa                                            22

<210> SEQ ID NO 13
<211> LENGTH: 416
<212> TYPE: DNA
<213> ORGANISM: Listeria rnpB consensus

<400> SEQUENCE: 13
taagaataaa tgaataacgt tcggataatc gctgtttttct tatggaagca gaggaaagtc   60
catgctcgca cggtgctgtg atgcccgtag tgatcgtgcc tggtcaaaca ataagccagg  120
gcattccgga gttttccggt ttgacggcag gtgaatgacc taagtcttcg agatatggtc  180

```
ttataacctt gaaggtgcca cagtgacgaa gttccggcag aaatgctcgg aagtggaacg      240
aggtaaaccc cacgagcgag aaactcaaac ttatggtagg ggcactttc ccgaggaatc      300 aagaacgagg gacgaggcgc gaatgtattt tcgtgcagat agatggttat ctctttacta     360
ttaccctgta tatagtaaag aacagaacat ggcttacaga gcgttattta caggat         416
```

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14

```
cactgggtag taacggaaat tgtagc                                          26
```

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15

```
aaccaatact tagcggaatc attaatc                                         27
```

<210> SEQ ID NO 16
<211> LENGTH: 141
<212> TYPE: DNA
<213> ORGANISM: Listeria rfn consensus

<400> SEQUENCE: 16

```
aaacgaaaaa ggtctgccaa catcttctcc catccagact atactgtcgg tcctggaatt     60
acaccagagt caactgctaa aaagcagat cgtggacttt aaccaccggt cgggaattgc     120
accctgcccc gaagatgaac g                                              141
```

<210> SEQ ID NO 17
<211> LENGTH: 504
<212> TYPE: DNA
<213> ORGANISM: Listeria monocytogenes

<400> SEQUENCE: 17

```
aagctggacg ataacgaata ggtatgctag tataagtaag ttaagaataa atgaataacg     60
ttcggataat cgctgttttc ttatggaagc agaggaaagt ccatgctcgc acggtgctgt    120
gatgcccgta gtgatcgtgc ctggtcaaac aataagccag ggcattccgg atttccggtt    180
tgacggcagt gaatgacct aagtcttcgg atatggtctt ataaccttga aggtgccaca     240
gtgacgaagt tccggcagaa atgctcggaa gtggaacgag gtaaacccca cgagcgagaa    300
actcaaactt atggtagggg cacttttccc gaggaatcaa gaacaaggga cgaggcgcaa    360
atgtattttt gcgcagatag atggttatct ctttactatt accctgtacg tagtaaagaa    420
cagaacatgg cttacagagc gttatttaca ggatttaatt taacattgaa ggctgtttta    480
gaaggccgga gcgcaagttt taag                                           504
```

<210> SEQ ID NO 18
<211> LENGTH: 508
<212> TYPE: DNA

<213> ORGANISM: Listeria innocua

<400> SEQUENCE: 18

```
tagctggacg ataacgaata ggtatgctag tataagtaag ttaagaataa atgaataacg      60
ttcggataat cgctgttttc ttatggaagc agaggaaagt ccatgctcgc acggtgctgt     120
gatgcccgta gtgatcgtgc ctggtcaaac aataagccag ggcattccgg atttccggtt     180
tgacggcagg tgaatgacct aagtcttcgg atatggtctt ataaccttga aggtgccaca     240
gtgacgaagt tccggcagaa atgctcggaa gtggaacgag gtaaacccca cgagcgagaa     300
actcaaactt atggtagggg cacttttccc gaggaatcaa gaacaaggga cgaggcgcaa     360
atgtattttt gtgcagatag atggttatct ctttactatt accctgtatg tagtaaagaa     420
cagaacatgg cttacagagc gttatttaca ggattaatt  taacattgaa ggctgtttta     480
gaaggccgga gcgcaagttt taaggtgt                                        508
```

<210> SEQ ID NO 19
<211> LENGTH: 426
<212> TYPE: DNA
<213> ORGANISM: Listeria seeligeri

<400> SEQUENCE: 19

```
ttaagaaaaa atgaataacg ttcggataat cgctgttttc ttagggaagc agaggaaagt      60
ccatgctcgc acggtgctgt gatgcccgta gtgatcgtgc ctggtcaaac aataagccag     120
ggcattccgg tgttttccgg tttgacggca ggtgaatgac ctaagtcttt tagatatggt     180
cttataaccct tgaaggtgcc acagtgacga agttccggca gaaatgctcg gaagtggaac     240
gaggtaaacc ccacgagcga gaaactcaaa cttatggtag gggcactttt cccgaggaat     300
caagaacgag ggacgaggtg cgaatttatt ttcgcgcaga tagatggtta tctcttact      360
attaccctgt atatagtaaa gaacagaaca tggcttacag agcgttattt gcaggatgaa     420
tttaac                                                                426
```

<210> SEQ ID NO 20
<211> LENGTH: 504
<212> TYPE: DNA
<213> ORGANISM: Listeria welshimeri

<400> SEQUENCE: 20

```
atagctggac gataacgact aggtgtgcta gtataagtaa gttaagaata atgaataac       60
gttcggataa tcgctgtttt cttttgaaaa cagaggaaag tccatgctcg cacggtgctg     120
tgatgcccgt agtgatcgtg cctggtcaaa caataagcca gggcattccg gatttccggt     180
ttgacggcag gtgaatgacc taagtcttcg gatatggtct tataaccttg aaggtgccac     240
agtgacgaag ttccggcaga aatgctcgga gtggaacga ggtaaacccc acgagcgaga      300
aactcaaact tatggtaggg gcacttttcc cgaggaatca agaacgaggg acgaggtacg     360
aatgaatttt cgtgcagata gatggttatc tctttgctat taccctgtat atagtaaaga     420
acagaacatg gcttacagag cgttatttac aggattaatt taacattgaa ggctgtttta     480
gaaggccgga gcgcaagttt taag                                            504
```

<210> SEQ ID NO 21
<211> LENGTH: 411
<212> TYPE: DNA
<213> ORGANISM: Listeria ivanovii

<400> SEQUENCE: 21

```
aaatgaataa cgttcggata atcgctgttt tcctaggaaa gcagaggaaa gtccatgctc      60
gcacggtgct gtgatgcccg tagtgatcgt gcctggtcaa acaataagcc agggcattcc     120
ggatttccgg tttgacggca ggtgaatgac ctaagtctac tagatatggt cttataacct     180
tgaaggtgcc acagtgacga agttccggca gaaatgctcg gaagtggaac gaggtaaacc     240 ccacagagcga gaaactcaaa cttatggtag gggcactttt cccgaggaat caagaacgag     300
ggacgaggcg cgaatttatt ttcgtgcaga tagatggtta tctctttact attaccctgt     360
atatagtaaa gaacagaaca tggcttacag agcgttattt acaggatgaa t              411
```

<210> SEQ ID NO 22
<211> LENGTH: 485
<212> TYPE: DNA
<213> ORGANISM: Listeria monocytogenes

<400> SEQUENCE: 22

```
ccaagaaccg ccacacttac aaaaaccttc attgaataat tcttcattgt catttctccc      60
ttgatgttca ccaagaagcg agtgacatca ctagacgaat gcaacccaag caaataaaaa     120
acctcaactg aaaagagttg agggagagtt tgtgaatgaa taaacaagaa ccggatactc     180
aaataagcat cacagcttgc taacacatgc tcgtgaagac aaacgaaaag gtctgccaac     240
atcttctccc atccagacta tactgtcggt cctggaatta caccagagtc aactgctaaa     300
aaagcagatc gtggactta accaccggtc gggaattgca ccctgcccg aagatgaacg     360 aatattttat tacaattttc attttaccat gaaaaaaatt tttggcaagc acttttgtat     420
attttttcac gtaagcgctt tctatctaaa ttaaataaaa actagctgct tagctagttt     480
ttatt                                                                 485
```

<210> SEQ ID NO 23
<211> LENGTH: 490
<212> TYPE: DNA
<213> ORGANISM: Listeria innocua

<400> SEQUENCE: 23

```
aatgctaaag taccaaagaa ccgccacact tacaaaaacc ttcattgaat aattcttcat      60
tgtcatttct cccttgatgt tcaccaagaa gcgagtgaca tcactaaacg aatgcaaccc     120
aagcaaataa aaaacctcaa ctaaaaaaag tcgagggaga gtttgtgatt aattaaacaa     180
gcactgaata ctcaaataag catcacagct tgctaacaca tgctcgtgaa gacaaacgaa     240
aaggtctgcc aacatcttct cccatccaga ctatactgtc ggtcctggaa ttacaccaga     300
gtcaactgct aagaaagcag atcgtggact ttaaccaccg gtcgggaatt gcaccctgcc     360
ccgaagatga acgaatattt tattacaatt tcattttac catgaaaata ttttttcgca     420
agtccttttg tatattttt cacgtaagcg ctttcttagt tacaaaaata aaaccacga     480 tgattatctg                                                            490
```

<210> SEQ ID NO 24
<211> LENGTH: 460
<212> TYPE: DNA
<213> ORGANISM: Listeria seeligeri

<400> SEQUENCE: 24

```
tcctagcacc gccacactta caaaaacctt cattgaataa ttcttcattg tcatttctcc      60
cttgatgttc atcaaaagaa gcgagtgaca tcacttaacg aatgcaaccc aagcaaataa     120
```

```
aaaacctcaa ctaaaaaagt tgagggagag tttgtgaata aataaacaaa cgttagatac    180
tcaaataagc atcttagctt gctcacacat gctcgtgaag acaaacgaaa aaggtctgtc    240
aacatcttct cccatccaga ctatactgtc ggtcctggaa ttacaccaga gtcaactgcc    300
aaaaaagcag atcgtggact ttaaccaccg gtcgggaatt gcaccctgcc ccgaagatga    360
acgaatattt tcttacaatt tttatttttac catgaataaa tattttcgca agcccttttg    420 tatattttt cacgtaagcg ctttcttata taaacaaaca                           460
```

<210> SEQ ID NO 25
<211> LENGTH: 451
<212> TYPE: DNA
<213> ORGANISM: Listeria welshimeri

<400> SEQUENCE: 25

```
acgcttacaa aaaccttcat tgaataattc ttcattgtca tttctccctt gatgttcacc     60
aagaagcgag tgacatcact taacgaatgc aacccaagca aataaaaaac ctcaactaaa    120 aaagttgag ggagagtttg tgaataaata acaagaaca gaatacttaa ataagcatcc     180
aagcttgcta ccacatgctc gtgaagacaa acgaaaaggt ctgccaacat cttctcccat    240
ccagactata ctgtcggtcc tggaattaca ccagagtcaa ctgctaaaaa gcagatcgtg    300
gactttaacc accggtcggg aattgcaccc tgccccgaag atgaacgaat attttattac    360
aatttttatt ttaccatgaa aaatttttt cgcaagccat tttgtatatt ttttcacgta    420
agcgctttct tataaaagaa acgaaaaacc a                                   451
```

<210> SEQ ID NO 26
<211> LENGTH: 431
<212> TYPE: DNA
<213> ORGANISM: Listeria ivanovii

<400> SEQUENCE: 26

```
gaataattct tcattgtcat ttctcccttg atgttcacca agaagtgagt gacgtcattt     60
aacgaatgca acccaagcaa ataaaaaacc tcaactaaaa aaagttgagg gagagtttgt    120
gaaacaataa acaaacatta gatgctcaaa taaacatcac agcttgctaa cacatgctcg    180
tgaagacaaa cgaaaaggtc tgccaacatc ttctcccatc cagactatac tgtcggtcct    240
ggaattacac cagagtcaac tgctaaaaaa gcagatcgtg gactttaacc accggtcggg    300
aattgcaccc tgccccgaag atgaacgaat attttcttac aaattttatt ttaccatgaa    360
taaatatttt cgcaagtcct tttgtatatt ttttcacgtg agcgttttct taattattcc    420
aataaaaaac c                                                        431
```

What is claimed is:

1. An isolated nucleic acid molecule selected from the group consisting of
   a) SEQ ID NO 1: 5'-AAAATACATTCGCGCCTCGTCCCT-3',
   b) SEQ ID NO 3: 5'-CAGATAGATGGTTATCTCTTTACTATTACCCTGTATATAGTAAAG -3',
   c) SEQ ID NO 6: 5'-CACGAAAATACATTTGCGCCTCGTCCCT-3',
   d) full complement sequences to SEQ ID NO's. 1, 3, or 6, and
   e) full reverse complements to SEQ ID NO 3.

2. A method for detecting nucleic acid of *Listeria* in a test sample, the method comprising:
   (i) providing a test sample containing bacterial nucleic acid, wherein the nucleic acid is accessible to primers or probe(s);
   (ii) providing at least one nucleic acid molecule of claim 1 for use as either a primer for a PCR reaction or a probe for a hybridization reaction; and
   (iii) performing a PCR reaction and/or a hybridization reaction on said bacterial genomic DNA using said primer or probe to target

```
                                              Seq ID NO 13
5'-TAAGAATAAATGAATAACGTTCGGATAATCGCTGTTTTCTTATGGAA

GCAGAGGAAAGTCCATGCTCGCACGGTGCTGTGATGCCCGTAGTGATCGT

GCCTGGTCAAACAATAAGCCAGGGCATTCCGGAGTTTTCCGGTTTGACGG
```

```
                                              -continued
CAGGTGAATGACCTAAGTCTTCGAGATATGGTCTTATAACCTTGAAGGTG

CCACAGTGACGAAGTTCCGGCAGAAATGCTCGGAAGTGGAACGAGGTAAA

CCCCACGAGCGAGAAACTCAAACTTATGGTAGGGGCACTTTTCCCGAGGA

ATCAAGAACGAGGGACGAGGCGCGAATGTATTTTCGTGCAGATAGATGGT

TATCTCTTTACTATTACCCTGTATATAGTAAAGAACAGAACATGGCTTAC

AGAGCGTTATTTACAGGAT-3
```
and

```
                                              Seq ID NO 16
5'-AAACGAAAAAGGTCTGTCCAACATCTTCTCCCATCCAGACTATACTG

TCGGTCCTGGAATTACACCAGAGTCAACTGCTAAAAAAGCAGATCGTGGA

CTTTAACCACCGGTCGGGAATTGCACCCTGCCCCGAAGATGAACG-3'.
```

3. An assay kit for the detection of *Listeria* comprising an isolated nucleic acid molecule selected from the group consisting of
   a) SEQ ID NO 1: 5'-AAAATACATTCGCGCCTCGTCCCT-3',
   b) SEQ ID NO 3: 5'-CAGATAGATGGTTATCTCTTTACTATTACCCTGTATATAGTAAAG-3',
   c) SEQ ID NO 6: 5'-CACGAAAATACATTTGCGCCTCGTCCCT-3',
   d) full complement sequences to SEQ ID NO's 1, 3, or 6, and
   e) full reverse complements to SEQ ID NO 3.

* * * * *

UNITED STATES PATENT AND TRADEMARK OFFICE
CERTIFICATE OF CORRECTION

PATENT NO. : 7,439,022 B2  
APPLICATION NO. : 11/153309  
DATED : October 21, 2008  
INVENTOR(S) : Hayashi Page 1 of 1

It is certified that error appears in the above-identified patent and that said Letters Patent is hereby corrected as shown below:

On title page, Col. 2 (Other Publications), Line 1, delete "Buck e al.," and insert -- Buck et al., --.

In Col. 34, Line 11, Claim 2, delete "3" and insert -- 3' --.

In Col. 34, Line 14, Claim 2, delete "5'-AAACGAAAAGGTCTGTCC" and insert -- 5'-AAACGAAAAGGTCTGCC --.

Signed and Sealed this

Seventeenth Day of February, 2009

JOHN DOLL  
*Acting Director of the United States Patent and Trademark Office*